United States Patent [19]

Bannister

[11] 4,031,304

[45] June 21, 1977

[54] PROCESS FOR PREPARING LINCOMYCIN DERIVATIVES

[75] Inventor: Brian Bannister, Kalamazoo, Mich.

[73] Assignee: The Upjohn Company, Kalamazoo, Mich.

[22] Filed: Jan. 30, 1976

[21] Appl. No.: 653,938

[52] U.S. Cl. .................................. 536/11; 536/4
[51] Int. Cl.² ............................................ C07H 15/16
[58] Field of Search .................. 260/210 L; 536/11

[56] References Cited
U.S. PATENT DOCUMENTS 3,689,474  9/1972  Kagan et al. ................... 260/210 L
3,767,649  10/1973  Bannister ........................ 260/210 L
3,790,560  2/1974  Bannister ........................ 260/210 L

*Primary Examiner*—Johnnie R. Brown
*Attorney, Agent, or Firm*—William G. Jameson; Sidney B. Williams, Jr.; Roman Saliwanchik

[57] ABSTRACT

Alkyl 7-deoxy-7-ω-substituted alkylthio-α-thiolincosaminides useful as intermediates for preparing antibacterially active 7-deoxy-7-ω-substituted alkylthiolincomycins are prepared by heating alkyl N-acyl-6,7-aziridino-6-deamino-7-deoxy-α-thiolincosaminides with an appropriate thiol in the presence of an anhydrous lower hydrocarbon carboxylic acid.

18 Claims, No Drawings

PROCESS FOR PREPARING LINCOMYCIN DERIVATIVES

BRIEF DESCRIPTION OF THE INVENTION

This invention relates to methods for making alkyl (7R,S) 7-deoxy-7-ω-substituted alkylthio-α-thiolincosaminides of Formula I:

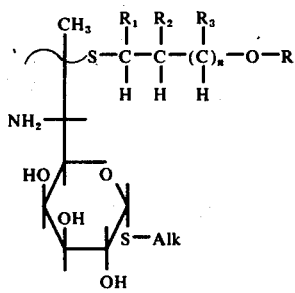

wherein Alk is alkyl of not more than 4 carbon atoms, for example, methyl, ethyl, propyl, isopropyl, butyl, sec.- butyl, isobutyl, and tert.-butyl; $R_1$ is hydrogen, methyl or ethyl; $R_2$ is hydrogen, methyl or ethyl; $R_3$ is hydrogen, methyl or ethyl; n is 0 or 1; and R is hydrogen, alkyl of 1 to 6 carbon atoms, inclusive, or aralkyl of 7 to 12 carbon atoms, inclusive.

The wavy line joining the substituent to the carbon atoms at position number 7 in Formulae I, IVa, IVb, V, and VII indicates that the compounds exist in both (7R) and (7S) epimeric forms.

The wavy line joining the methyl group and the hydrogen to the carbon atom at position number 7 in Formulae IIa, IIb and VI indicates that the compounds exist in both (6R,7R) and (6R,7S) epimeric forms.

The term "carboxacyl" as used throughout the specification and claims means the acyl radical of a hydrocarbon carboxylic acid or of a hydrocarbon carboxylic acid substituted with an inert group. Preferred as carboxacyl groups are the acyl radicals of hydrocarbon carboxylic acids and inert group substituted hydrocarbon carboxylic acids having from 2 to about 18 carbon atoms, inclusive, in their structure. Representative of such carboxyacyl groups are those of formula:

wherein E is hydrocarbyl of from 1 to about 17 carbpon atoms, inclusive, or hydrocarbyl of from 1 to 17 carbon atoms, inclusive, wherein a hydrogen atom has been replaced with an inert substituent group. Illustrative of acyl radicals of a hydrocarbon carboxylic acid wherein E is hydrocarbyl are the acyl radicals of (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids and the like; (b) saturated or unsaturated, alicyclic carboxylic acids, for example, cyclobutanecarboxylic acid, cyclopentanecarboxylic acids, cyclopentenecarboxylic acid, methylcyclopentenecarboxylic acid, cyclohexanecarboxylic acid, dimethylcyclohexenecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropionic acid, and naphthylacetic acid, and the like.

The term "hydrocarbon carboxylic acid substituted with an inert group" is used herein to mean a hydrocarbon carboxylic acid wherein one or more hydrogen atoms attached directly to a carbon atom have been replaced with a group inert to reaction under the conditions hereinafter described for preparing compounds (I) of the invention. Illustrative of such substituent groups are halo-, nitro-, hydroxy-, amino-, cyano-, thiocyano-, or alkoxy-groups. Illustrative of halo-, nitro-, hydroxy-, amino-, cyano-, thiocyano-, and alkoxy-substituted hydrocarbon carboxylic acids are mono-, di-, and trichloroacetic acid; α- and β-chloropropionic acid; α- and γ-bromobutyric acid; α- and δ iodovaleric acid; mevalonic acid; 2- and 4-chlorocyclohexanecarboxylic acid; shikimic acid; 2-nitro-1-methylcyclobutanecarboxylic acid; 1,2,3,4,5,6-hexachlorocyclohexanecarboxylic acid; 3-bromo-2-methylcyclohexanecarboxylic acid; 4- and 5-bromo-2-methylcyclohexanecarboxylic acid; 5- and 6-bromo-2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid; 5,6-dibromo-2-methylcyclohexanecarboxylic acid; 3-bromo-3-methylcyclohexanecarboxylic acid; 6-bromo-3-methylcyclohexanecarboxylic acid; 1,6-dibromo-3-methylcyclohexanecarboxylic acid; 2-bromo-4-methylcyclohexanecarboxylic acid; 1,2-dibromo-4-methylcyclohexanecarboxylic acid; 3-bromo-2,2,3-trimethylcyclopentanecarboxylic acid; 1-bromo-3,5-dimethylcyclohexanecarboxylic acid; homogentisic acid; o-, m-, and p-chlorobenzoic acid; anisic acid; salicyclic acid; p-hydroxybenzoic acid; β-resorcylic acid; gallic acid, veratric acid, trimethoxybenzoic acid; trimethoxycinnamic acid; 4,4'-dichlorobenzilic acid; o-, m-, and p-nitrobenzoic acid; cyanoacetic acid; 3,4- and 3,5-dinitrobenzoic acids, 2,4,6-trinitrobenzoic acid; thiocyanoacetic acid; cyanopropionic acid; lactic acid; ethoxyformic acid (ethyl hydrogen carbonate); butyloxyformic acid; pentyloxyformic acid, hexyloxyformic acid; dodecyloxyformic acid; hexadecyloxyformic acid and the like.

The term "aralkyl" as used in the specification and claims means an aralkyl of from 7 to 12 carbon atoms, inclusive. Illustrative of aralkyl of from 7 to 12 carbon atoms, inclusive, are benzyl, phenethyl, α-phenylpropyl, and α-naphthylmethyl. The invention comprises methods of preparing the compounds of Formula I and Formula IV. These methods of preparation will be described in greater detail hereinafter.

DETAILED DESCRIPTION OF THE INVENTION

The process of the invention is carried out according to the following procedures.

PROCESS A

The compounds of Formula I can be obtained by heating an alkyl N-acyl-6,7-aziridino-6-deamino-7-deoxy-α-thiolincosaminide of the formula:

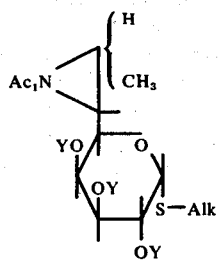

IIa in which $Ac_1$ and Y are carboxacyl, and Alk is alkyl of 1 to 4 carbon atoms, inclusive, with a thiol of the formula:

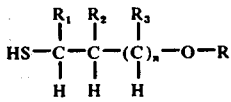

III wherein $R_1$ is hydrogen, methyl or ethyl; $R_2$ is hydrogen, methyl or ethyl; $R_3$ is hydrogen, methyl or ethyl; n is 0 or 1; and R is hydrogen, alkyl of 1 to 6 carbon atoms, inclusive, or aralkyl of 7 to 12 carbon atoms, inclusive, in the presence of glacial acetic acid or other anhydrous lower hydrocarbon carboxylic acid. Opening of the aziridine ring is thus effected yielding an acylated alkyl 7-deoxy-7-substituted-α-thiolincosaminide of the following formula:

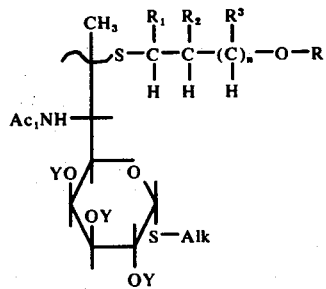

IVa wherein $Ac_1$, Y, Alk, n, R, $R_1$, $R_2$ and $R_3$ are as defined above.

The acyl groups ($Ac_1$ and Y) are then removed by hydrazinolysis, for example, by following the procedure set forth in U.S. Pat. No. 3,179,565, to obtain the corresponding compound of Formula I:

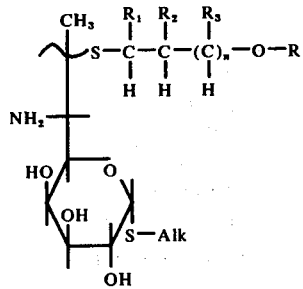

I wherein Alk, n, R, $R_1$, $R_2$ and $R_3$ are as defined above.

The compounds of Formula I are useful for the same purposes as methyl α-thiolincosaminide (methyl 6-amino-6,8-dideoxy-1-thio-D-erythro-α-D-galacto-octopyranoside, α-MTL) as disclosed in U.S. Pat. No. 3,380,992 and as methyl 6-amino-7-chloro-6,7,8-trideoxy-1-thio-L-threo-and D-erythro-α-D-galacto-octopyranosides (U.S. Patents 3,496,163 and 3,502,648), and moreover can be acylated with trans-1-methyl-4-propyl-L-2-pyrrolidine carboxylic acid to form 7-deoxy-7-(ω-substituted alkylthio)lincomycins and with other L-2-pyrrolidine carboxylic acids as disclosed in these patents, or with an N-(2-hydroxyethyl)-L-2-pyrrolidine carboxylic acid to form compounds of the formula:

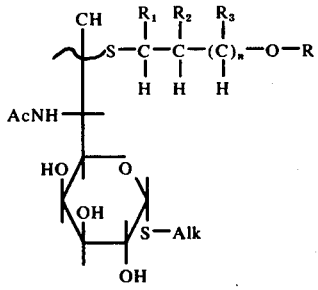

V wherein Alk, n, R, $R_1$, $R_2$ and $R_3$ are as given and Ac is L-2-pyrrolidinecarboxacyl or an N-methyl, N-ethyl, or N-(2-hydroxyethyl)-L-2-pyrrolidinecarboxacyl any or all of which can be substituted in the 4-position with lower alkyl or lower alkylidene.

The compounds of Formula IIa undergo thiolysis when heated with a suitable thiol in glacial acetic acid or anhydrous benzoic acid or other anhydrous lower hydrocarbon carboxylic acid.

Suitable thiols have the formula:

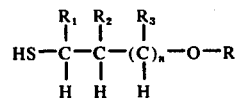

III wherein $R_1$ is hydrogen, methyl or ethyl; $R_2$ is hydrogen, methyl or ethyl; $R_3$ is hydrogen, methyl or ethyl; n is 0 or 1; and R is hydrogen, alkyl of 1 to 6 carbon atoms, inclusive, or aralkyl of 7 to 12 carbon atoms, inclusive.

Illustrative examples of suitable thiols according to the invention are

TABLE I 2-hydroxyethane-1-thiol,
3-hydroxypropane-1-thiol,
2-hydroxypropane-1-thiol,
1-hydroxypropane-2-thiol,
3-hydroxybutane-1-thiol,
1-hydroxybutane-3-thiol,
2-(hydroxymethyl)propane-1-thiol,
2-hydroxybutane-1-thiol,
1-hydroxybutane-2-thiol,
3-hydroxypentane-1-thiol,
2-(hydroxymethyl)butane-1-thiol,
1-hydroxypentane-3-thiol,
2-methoxyethane-1-thiol,
3-methoxypropane-1-thiol,
2-methoxypropane-1-thiol,
1-methoxypropane-2-thiol, 3-methoxybutane-1-thiol,
1-methoxybutane-3-thiol,
2-(methoxymethyl)propane-1-thiol,
2-methoxybutane-1-thiol,
1-methoxybutane-2-thiol,
3-methoxypentane-1-thiol,
2-(methoxymethyl)butane-1-thiol,
1-methoxypentane-3-thiol,
2-ethoxyethane-1-thiol,
3-ethoxypropane-1-thiol,
2-ethoxypropane-1-thiol,
1-ethoxypropane-2-thiol,
3-ethoxybutane-1-thiol,
1-ethoxybutane-3-thiol,
2-(ethoxymethyl)propane-1-thiol,
2-ethoxybutane-1-thiol,
1-ethoxybutane-2-thiol,
3-ethoxypentane-1-thiol,
2-(ethoxymethyl)butane-1-thiol,
1-ethoxypentane-3-thiol,
2-propoxyethane-1-thiol,
3-propoxypropane-1-thiol,
2-propoxypropane-1-thiol,
1-propoxypropane-2-thiol,
3-propoxybutane-1-thiol,
1-propoxybutane-3-thiol,
2-(propoxymethyl)propane-1-thiol,
2-propoxybutane-1-thiol,
1-propoxybutane-2-thiol,
3-propoxypentane-1-thiol,
2-(propoxymethyl)butane-1-thiol,
1-propoxypentane-3-thiol,
2-butoxyethane-1-thiol,
3-butoxypropane-1-thiol,
2-butoxypropane-1-thiol,
1-butoxypropane-2-thiol,
3-butoxybutane-1-thiol,
1-butoxybutane-3-thiol,
2-(butoxymethyl)propane-1-thiol,
2-butoxybutane-1-thiol,
1-butoxybutane-2-thiol,
3-butoxypentane-1-thiol,
2-(butoxymethyl)butane-1-thiol,
1-butoxypentane-3-thiol,
2-pentyloxyethane-1-thiol,
3-pentyloxypropane-1-thiol,
2-pentyloxypropane-1-thiol,
1-pentyloxypropane-2-thiol,
3-pentyloxybutane-1-thiol,
1-pentyloxybutane-3-thiol,
2-(pentyloxymethyl)propane-3-thiol,
2-pentyloxybutane-1-thiol,
1-pentyloxybutane-2-thiol,
3-pentyloxypentane-1-thiol,
2-(pentyloxymethyl)butane-1-thiol,
1-pentyloxypentane-3-thiol,
2-hexyloxyethane-1-thiol,
3-hexyloxypropane-1-thiol,
2-hexyloxypropane-1-thiol,
1-hexyloxypropane-2-thiol,
3-hexyloxybutane-1-thiol,
1-hexyloxybutane-3-thiol,
2-(hexyloxymethyl)propane-1-thiol,
2-hexyloxybutane-1-thiol,
1-hexyloxybutane-2-thiol,
3-hexyloxypentane-1-thiol,
2-(hexyloxymethyl)butane-1-thiol,
1-hexyloxypentane-3-thiol, 2-benzyloxyethane-1-thiol,
3-benzyloxypropane-1-thiol,
2-benzyloxypropane-1-thiol,
1-benzyloxypropane-2-thiol,
3-benzyloxybutane-1-thiol,
1-benzyloxybutane-3-thiol,
2-(benzyloxymethyl)propane-1-thiol,
2-benzyloxybutane-1-thiol,
1-benzyloxybutane-2-thiol,
3-benzyloxypentane-1-thiol,
2-(benzyloxymethyl)butane-1-thiol,
1-benzyloxypentane-3-thiol,
2-[(ar-methylbenzyl)oxy]ethane-1-thiol,
3-[(ar-methylbenzyl)oxy]propane-1-thiol,
2-[(ar-methylbenzyl)oxy]propane-1-thiol,
1-[(ar-methylbenzyl)oxy]propane-2-thiol,
3-[(ar-methylbenzyl)oxy]butane-1-thiol,
1-[(ar-methylbenzyl)oxy]butane-3-thiol,
2-[(ar-methylbenzyl)oxy]methyl propane-1-thiol,
2[(ar-methylbenzyl)oxy]butane-1-thiol,
1-[(ar-methylbenzyl)oxy]butane-2-thiol,
3-[(ar-methylbenzyl)oxy]pentane-1-thiol,
2-[(armethylbenzyl)oxy]methyl butane-1-thiol,
1-[(ar-methylbenzyl)oxy]pentane-3-thiol,
2-[(ar-ethylbenzyl)oxy]ethane-1-thiol,
3-[(ar-ethylbenzyl)oxy]propane-1-thiol,
2-[(ar-ethylbenzyl)oxy]propane-1-thiol,
1-[(ar-ethylbenzyl)oxy]propane-2-thiol,
3-[(ar-ethylbenzyl)oxy]butane-1-thiol,
1-[(ar-ethylbenzyl)oxy]butane-3-thiol,
2-[(ar-ethylbenzyl)oxy]methyl propane-1-thiol,
2-[(ar-ethylbenzyl)oxy]butane-1-thiol,
1-[(ar-ethylbenzyl)oxy]butane-2-thiol,
3-[(ar-ethylbenzyl)oxy]butane-1-thiol,
2-[(ar-ethylbenzyl)oxy]methyl butane-1-thiol,
1-[-(ar-ethylbenzyl)oxy]pentane-3-thiol,
2-[(ar-methyl-2-phenyl)ethoxy]ethane-1-thiol,
3-[(ar-methyl-2-phenyl)ethoxy]propane-1-thiol,
2-([ar-methyl-2-phenyl)ethoxy]propane-1-thiol,
1-[(ar-methyl-2-phenyl)ethoxy]propane-2-thiol,
3-[(ar-methyl-2-phenyl)ethoxy]butane-1-thiol,
1-[(ar-methyl-2-phenyl)ethoxy]butane-3-thiol,
2-[(ar-methyl-2-phenyl)ethoxy]methyl propane-1-thiol,
2-[(ar-methyl-2-phenyl)ethoxy]butane-1-thiol,
1-[(ar-methyl-2-phenyl)ethoxy]butane-2-thiol,
3-[(ar-methyl-2-phenyl)ethoxy]pentane-1-thiol,
2-[(ar-methyl-2-phenyl)methoxy]methyl butane-1-thiol,
1-[(ar-methyl-2-phenyl)ethoxy]pentane-3-thiol,
2-[(ar-ethyl-2-phenyl)ethoxy]ethane-1-thiol,
3-[(ar-ethyl-2-phenyl)ethoxy]propane-1-thiol,
2-[(ar-ethyl-2-phenyl)ethoxy]propane-1-thiol,
1-[(ar-ethyl-2-phenyl)ethoxy]propane-2-thiol,
3-[(ar-ethyl-2-phenyl)ethoxy]butane-1-thiol,
1-[(ar-ethyl-2-phenyl)ethoxy]butane-3-thiol,
2-[(ar-ethyl-2-phenyl)ethoxy]methyl propane-1-thiol,
2-[(ar-ethyl-2-phenyl)ethoxy]butane-1-thiol,
1-[(ar-ethyl-2-phenyl)ethoxy]butane-2-thiol,
3-[(ar-ethyl-2-phenyl)ethoxy]pentane-1-thiol,
2-[(ar-ethyl-2-phenyl)ethoxy]methyl butane-1-thiol,
1-[(ar-ethyl-2-phenyl)ethoxy]pentane-3-thiol,
2-[(ar-methylnaphthyl)methoxy]ethane-1-thiol,
3-[(ar-methylnaphthyl)methoxy]propane-1-thiol,
2-(ar-methylnaphthyl)methoxy]propane-1-thiol,
1-[(arm-methylnaphthyl)methoxy]propane-2-thiol, 3-[(ar-methylnaphthyl)methoxy]butane-1-thiol,
1-[(ar-methylnaphthyl)methoxy]butane-3-thiol,
2- [(ar-methylnaphthyl)methoxy]methyl propane-1-thiol,
2-[(ar-methylnaphthyl)methoxy]butane-1-thiol,
1-[(ar-methylnaphthyl)methoxy]butane-2-thiol,
3-[(armethylnaphthyl)methoxy]pentane-1-thiol,
2- [ar-methylnaphthyl)methoxy]methyl butane-1-thiol,
1-[(ar-methylnaphthyl)methoxy]pentane-3-thiol,
2-[(2-naphthyl)ethoxy]ethane-1-thiol,
3-[(2-naphthyl)ethoxy]propane-1-thiol,
2-[(2-naphthyl)ethoxy]propane-1-thiol,
1-[(2-naphthyl)ethoxy]propane-2-thiol,
3-[(2-naphthyl)ethoxy]butane-1-thiol,
1-[(2-naphthyl)ethoxy]butane-3-thiol,
2- [(2-naphthyl)ethoxy]methyl propane-1-thiol,
2-[(2-naphthyl)ethoxy]butane-1-thiol,
1-[(2-naphthyl)ethoxy]butane-2-thiol,
3-[(2-naphthyl)ethoxy]pentane-1-thiol,
2- [(2-naphthyl)ethoxy]methyl butane-1-thiol, and
1-[(2-naphthyl)ethoxy]pentane-3-thiol.

The term "ar" as used in naming the thiols described in Table I denotes that the substituent is on the aromatic ring.

With any of the thiols described in Table I, the desired thiolysis can be obtained simply by heating an alkyl N-acetyl-6,7-aziridino-6-deamino-7-deoxy-α-thiolincosaminide with the appropriate thiol in glacial acetic acid or other anhydrous lower hydrocarbon carboxylic acid. The reaction proceeds satisfactorily under a broad range of temperature conditions, i.e., within a range of from about 25° C. to about 180° C. Preferably, the process of the invention is carried out within a temperature range of from about 60° C. to about 150° C. and most preferably within a temperature range of from about 80° C. to about 110° C. The proportions of reactants (IIa) and (III) are not critical to the process of reaction, but influence the yields of product compounds (I). The proportions employed may be stoichiometric, i.e., substantially equimolar. Optimum yields are obtained by employing the thiol reactant (III) in excess, i.e., a molar excess and preferably in a proportion of at least 2 molar equivalents, and most preferably within a range of from about 5 molar equivalents to about 60 molar equivalents. The reaction is acid catalyzed. Thus, the reaction is effected under acidic conditions such as are obtained with an anhydrous lower hydrocarbon carboxylic acid, such as glacial acetic acid. The anhydrous lower hydrocarbon carboxylic acid is advantageously employed in a molar proportion of from 1 to 7 relative to the acyl aziridine.

Advantageously, the above described reaction is carried out in the presence of a suitable organic solvent. A suitable organic solvent is defined for the purpose of this invention as an organic solvent which will at least partially solubilize the thiolincosaminide reactant (IIa) and which does not in any way adversely affect the desired course of the reaction. Illustrative of suitable organic solvents are dioxane, carbon tetrachloride, chloroform, methylene chloride, benzene, toluene, n-hexane and like organic solvents. Preferred as the organic solvent is an excess of thiol compound (III), i.e., in a proportion beyond that required for the above described reaction, provided said thiol compound (III) meets the above criteria for solubilizing reactant (IIa) at the temperature selected for carrying out the process.

In general, the above described reaction is complete in from about 1 to about 20 hours, depending upon the nature of the groups $Ac_1$, Y, R, $R_1$, $R_2$, and $R_3$ in the formulae (IIa) and (III). Completion of the reaction may be ascertained by conventional analytical procedures such as, for example, by vapor-phase chromatography, thin-layer chromatography and like procedures which will indicate the disappearance of starting compounds (IIa) and the appearance of the desired product compounds (IVa).

Upon completion of the reaction, the reaction mixture can be subjected to procedures well known in the art such as countercurrent distribution, chromatography, and solvent extraction or crystallization to isolate the reaction product, if desired.

Illustrative of anhydrous lower hydrocarbon carboxylic acids are dry lower alkanoic acids having 2 to 8 carbon atoms, inclusive, such as acetic acid, propionic acid and octanoic acid; arenoic acids having 7 to 8 carbon atoms, inclusive, such as benzoic acid and toluic acid. Preferred as the anhydrous hydrocarbon carboxylic acid is glacial acetic acid.

The reaction which occurs is conveniently illustrated by the schematic formulae:

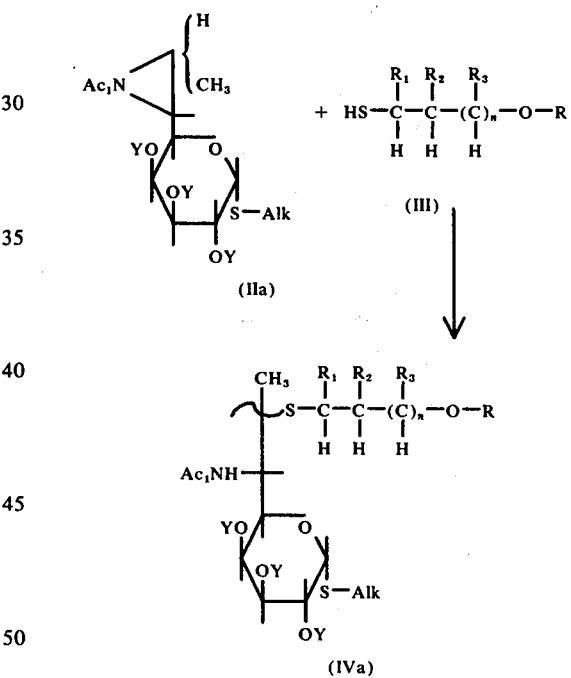

wherein $Ac_1$, Y, AlK, $R_1$, $R_2$, $R_3$, R and n are as defined above.

The starting compounds exist in two epimeric forms as follows:

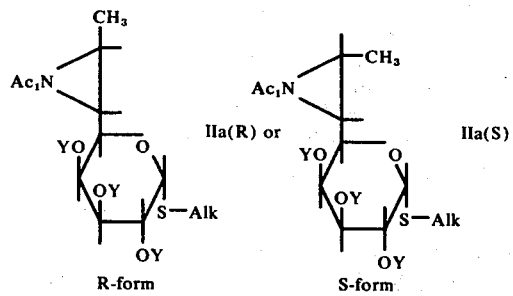

R-form      S-form

The R and S refer to the 7-position as the 6-position is always in the R-form. In the reaction an inversion takes place. For example, an alkyl (6R,7)R-N-acyl 6,7-aziridino-6-deamino-7-deoxy-α-thiolincosaminide is converted to the corresponding (7S)-derivative, as a result of the inversion of the (7R)-position in the (6R,7R)-form during the course of the reaction. This inversion which occurs is conveniently illustrated by the schematic formulae:

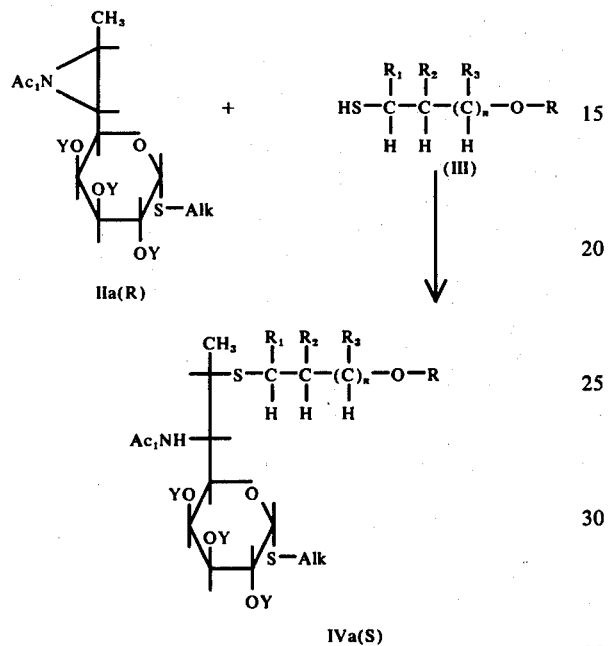

IIa(R)

IVa(S)

wherein $Ac_1$, Y, Alk, R, $R_1$, $R_2$, $R_3$ and n are as defined above. In a like manner, an alkyl (6R,7S)-N-acyl-6,7-aziridino-6-deamino-7-deoxy-α-thiolincosaminide is converted to the corresponding (7R)-derivative, as a result of the inversion of the (7S)-position in the (6R,7S)-form during the course of the reaction. This inversion is conveniently illustrated by the schematic formulae:

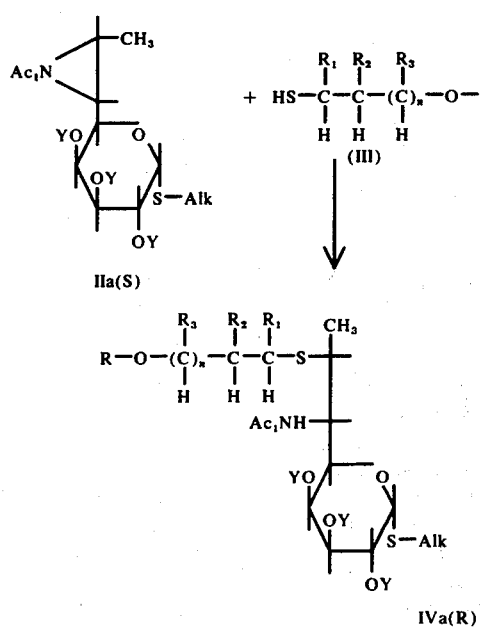

IIa(S)

IVa(R)

wherein $Ac_1$, Y, Alk, R, $R_1$, $R_2$, $R_3$ and n are as defined above.

The starting aziridino compounds of Formula IIa are well-known compounds, see for example U.S. Pat. Nos. 3,671,647 and 3,702,322, and are obtained by acylating a compound of the formula:

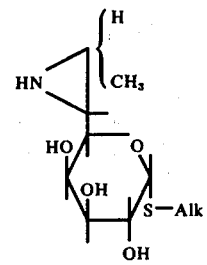

VI with a carboxacyl acylating agent, such as acetic anhydride or other lower alkanoic acid anhydride or benzoyl chloride or like carboxacyl halide, in a manner already known in the art. Since the amino and hydroxy groups acylate at different rates the N-acyl, $Ac_1$, and the O-acyl, Y, can be the same or different.

Inasmuch as these acyl groups ($Ac_1$ and Y) do not appear in the final product but are removed in the processing, it is immaterial what they are as long as they are carboxacyl.

The starting compounds of Formula VI can be prepared by the dehydrohalogenation of a compound of the formula:

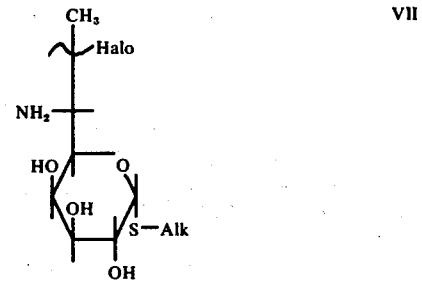

VII which are known in the art; U.S. Pat. 3,502,648. The dehydrohalogenation is effected by heating a compound of Formula VII in an inert solvent in the presence of an acid acceptor. A suitable process is to heat a reaction mixture of starting compound, anhydrous sodium carbonate and dimethylformamide at reflux for a short time, remove the solvent, and crystallize from a suitable solvent, for example, methanol. See U.S. Pat. No. 3,544,551.

By acylating the compounds of Formula I with an L-2-pyrrolidine carboxylic acid, compounds of Formula V in which Ac is the acyl of the L-2-pyrrolidine carboxylic acid are obtained. When Alk is methyl, n is O, R, $R_1$ and $R_2$ are hydrogen, and the L-2-pyrrolidinecarboxylic acid is trans-1-methyl-4-propyl-L-2-pyrrolidinecarboxylic acid and the configuration is (S), the compound is (7S)-7-deoxy-7-(2-hydroxyethylthio)-lincomycin.

PROCESS B

The compounds of Formula I can also be prepared by heating an alkyl N-acyl-6,7-aziridino-6-deamino-7-deoxy-α-thiolincosaminide of the formula:

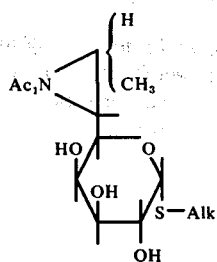

wherein Ac$_1$, Alk and the wavy lines have the meanings previously described to them, with a thiol of the formula:

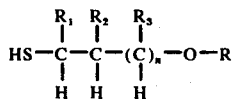

wherein R, R$_1$, R$_2$, R$_3$ and n are as previously defined, in the presence of glacial acetic acid or other anhydrous lower hydrocarbon carboxylic acid to form

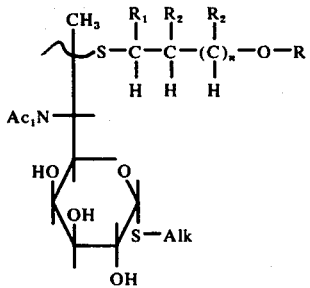

wherein Ac$_1$, Alk, R, R$_1$, R$_2$, R$_3$, and n are as previously defined, acylating the alcoholic hydroxyl groups of said compound with a carboxyacyl acylating agent, such as acetic anhydride or other lower alkanoic acid anhydride or benzoyl chloride or like carboxacyl halide to form the corresponding alkyl N-acyl-2,3,4-tri-O-acyl-7-deoxy-7-(ω-acyloxyalkylthio)-α-thiolincosaminide when R is hydrogen, alkyl N-acyl-2,3,4-tri-O-acyl-7-deoxy-7-(ω-alkoxyalkylthio)-α-thiolincosaminide when R is alkyl, or alkyl N-acyl-2,3,4-tri-O-acyl-7-deoxy-7-(ω-aralkoxyalkylthio)-α-thiolincosaminide when R is aralkyl, deacylating the latter to form the corresponding compound of Formula I:

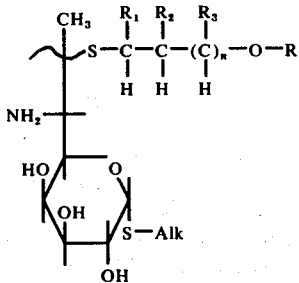

wherein Alk, n, R, R$_1$, R$_2$, and R$_3$ are as defined above.

With any of the thiols described in Table I of Process A, the desired thiolysis can be obtained simply by heating an alkyl N-acetyl-6,7-aziridino-6-deamino-7-deoxy-α-thiolincosaminide with the appropriate thiol in glacial acetic acid or other anhydrous lower hydrocarbon carboxylic acid. The reaction proceeds satisfactorily under a broad range of temperature conditions, i.e., within a range of from about about 25° C. to about 180° C. Preferably, the process of the invention is carried out within a temperature range of from about 60° C. to about 150° C. and most preferably within a temperature range of from about 80° C. to about 110° C. The proportions of reactants (IIb) and (III) are not critical to the process of reaction, but influence the yields of product compounds (I). The proportions employed may be stoichiometric, i.e., substantially equimolar. Optimum yields are obtained by employing the thiol reactant (III) in excess, i.e., a molar excess and preferably in a proportion of at least 2 molar equivalents, and most preferably within a range of from about 5 molar equivalents to about 60 molar equivalents. The reaction is acid catalyzed. Thus, the reaction is effected under acidic conditions such as are obtained with an anhydrous lower hydrocarbon carboxylic acid, such as glacial acetic acid. The anhydrous lower hydrocarbon carboxylic acid is advantageously employed in a molar proportion of from 1 to 7 relative to the acyl aziridine.

Advantageously, the above described reaction is carried out in the presence of a suitable organic solvent. A suitable organic solvent is defined for the purpose of this invention as an organic solvent which will at least partially solubilize the thiolincosaminide reactant (IIb) and which does not in any way adversely affect the desired course of the reaction. Illustrative of suitable organic solvents are dioxane, carbon tetrachloride, chloroform, methylene chloride, benzene, toluene, n-hexane and like organic solvents. Preferred as the organic solvent is an excess of thiol compound (III), i.e., in a proportion beyond that required for the above described reaction, provided said thiol compound (III) meets the above criteria for solubilizing reactant (IIb) at the temperature selected for carrying out the process.

In general, the above described reaction is complete in from about 1 to about 20 hours, depending upon the nature of the groups Ac$_1$, R, R$_1$, R$_2$, and R$_3$ in the formulae (IIb) and (III). Completion of the reaction may be ascertained by conventional analytical procedures such as, for example, by vapor-phase chromatography, thin-layer chromatography and like procedures which will indicate the disappearance of starting compounds (IIB) and the appearance of the desired product compounds (IVb).

Upon completion of the thiolysis, the excess solvent and reactant (III) can be removed from the reaction mixture and without separating the intermediate compound of Formula (IVb) the reaction mixture is acylated with an acylating reagent selected from acyl halides and acid anhydrides of hydrocarbon carboxylic acids containing from 2 to 12 carbon atoms, inclusive, such as acetic anhydride, in a manner known in the art, to form the corresponding alkyl N-acyl-2,3,4-tri-O-acyl-7-deoxy-7-(ω-acyloxyalkylthio)-α-thiolincosaminide when R is hydrogen, alkyl N-acyl-2,3,4-tri-O-acyl-7-deoxy-7-(ω-alkoxyalkylthio)-α-thiolincosaminide when R is alkyl, or alkyl N-acyl-2,3,4-tri-O-acyl-7-deoxy-7-(ω-aralkoxyalkylthio)-α-thiolincosaminide when R is aralkyl.

Upon completion of the acylation, the reaction mixture can be subjected to procedures well known in the art such as countercurrent distribution, chromatography, and solvent extraction or crystallization to isolate the corresponding alkyl N-acyl-2,3,4-tri-O-acyl-7- deoxy-7-(ω-acyloxyalkylthio)-α-thiolincosaminide when R is hydrogen, alkyl N-acyl-2,3,4-tri-O-acyl-7-deoxy-7-(ω-alkoxyalkylthio)-α-thiolincosaminide when R is alkyl, or alkyl N-acyl-2,3,4-tri-O-acyl-7-deoxy-7-(ω-aralkoxyalkylthio)-α-thiolincosaminide when R is aralkyl. In a manner known in the art, the latter is deacylated to form the corresponding compound of Formula I.

The starting aziridino compounds of Formula IIb are known compounds and are obtained by acylating a compound of the formula (VI):

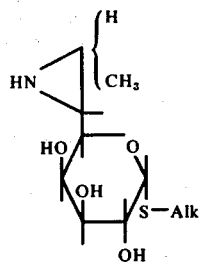

with a carboxacyl acylating agent, such as acetic anhydride or other lower alkanoic acid anhydride or benzoyl chloride or like carboxacyl halide.

The following examples are illustrative of the process of the present invention, but are not to be construed as limiting.

EXAMPLE 1

Part A-1 - Methyl (7S)-N-acetyl-2,3,4-tri-O-acetyl-7-deoxy-7-(2-methoxyethylthio)-α-thiolincosaminide

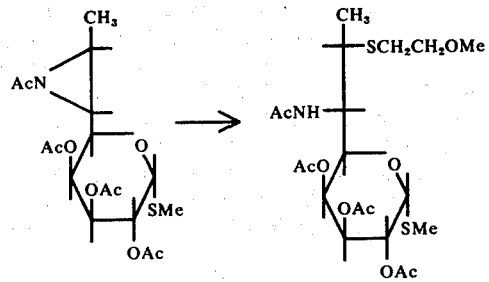

5.0 Grams (1 molar equivalent) of methyl (6R,7R)-N-acetyl-2,3,4-tri-O-acetyl-6,7-aziridino-6-deamino-7-deoxy-α-thiolincosaminide is dissolved in 50 grams (44 molar equivalents) of 2-methoxyethanethiol by stirring in an oil-bath at 100° C. 2,61 Grams (2.50 ml.; 3.5 molar equivalents) of glacial acetic acid are added, and the mixture heated at 100° C. for 17 hours with exclusion of moisture. At the end of this period, the volatile materials are removed from the reaction mixture by distillation under high vacuum (ca. 0.2 mm Hg) at a temperature of 80° C. (oil-bath temperature), giving a colorless solid residue showing by TLC [silica gel, acetone:Skellysolve B® (1:1 v/v)] a major zone of $R_f$ 0.48. TLC refers to thin layer chromatography and Skellysolve B® to essentially n-hexane, b.p. 60°–68° C., Skelly Oil Co., Inc.

The above colorless solid residue is subjected to countercurrent distribution in the system ethanol:water:ethyl acetate:cyclohexane (1:1:1:2, v/v) to yield a major product at a K value of 0.81. Combination of material from tubes 190–250, inclusive, after 500 transfers, and removal of the solvent gives 2.61 grams (43% yield) of methyl (7S)-N-acetyl-2,3,4-tri-O-acetyl-7-deoxy-7-(2-methoxyethylthio)-α-thiolincosaminide as a colorless solid. It is obtained as colorless needles upon crystallization from ethyl acetate, m.p. 225°–227° C., undepressed on admixture with material derived from 2-methoxyethyl methyl sulfide (Example 21, Part A-21 of U.S. Pat. No. 3,915,954) and identical with this compound in I.R. and N.M.R. spectra.

Part B-1 - Methyl (7S)-7-deoxy-7-(2-methoxyethylthio)-α-thiolincosaminide

Methyl (7S)-7-deoxy-7-(2-methoxyethylthio)-α-thiolincosaminide can be obtained from methyl (7S)-N-acetyl-2,3,4-tri-O-acetyl-7-deoxy-7-(2-methoxyethylthio)-α-thiolincosaminide by following the procedure of Example 1, Part B-1 of U.S. Pat. No. 3,915,954.

Part C-1 - (7S)-7-deoxy-7-(2-methoxyethylthio)lincomycin hydrochloride (7S)-7-deoxy-7-(2-methoxyethylthio)lincomycin hydrochloride can be obtained from methyl (7S)-7-deoxy-(2-methoxyethylthio)-α-thiolincosaminide by following the procedure of Example 1, Part C-1 of U.S. Pat. No. 3,915,954.

EXAMPLE 2

Part A-2 - Methyl (7S)-N-acetyl-2,3,4-tri-O-acetyl-7-deoxy-7-(2-hydroxyethylthio)-α-thiolincosaminide

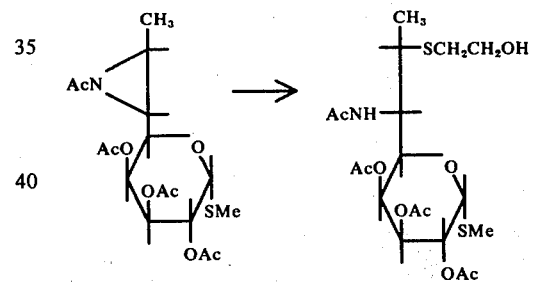

7.0 Grams (1 molar equivalent) of methyl (6R,7R)-N-acetyl-2,3,4-tri-O-acetyl-6,7-aziridino-6-deamino-7-deoxy-α-thiolincosaminide is dissolved in 70.0 grams (52 molar equivalents) of 2-hydroxyethanethiol by stirring in an oil bath at 100° C. 7.35 Grams (7.0 ml.; 7 molar equivaletns) of glacial acetic acid are added, and the mixture heated at 100° C. for 17 hours with the exclusion of moisture. At the end of this period, the volatile materials are removed from the reaction mixture by distillation under high vacuum (ca. 0.2 mm) at a temperature of 80° C. (oil-bath temperature), giving a semi-crystalline residue showing by TLC [silica gel, acetone:Skellysolve B® (1:1 v/v)] a major zone of $R_f$ 0.34.

The above semi-crystalline solid is subjected to countercurrent distribution in the system ethanol-water-ethyl acetate-cyclohexane (1:1:1:0.5, v/v/v/v) to yield a major product at a K value of 0.91. Combination of material from tubes 210–263 after the 500 transfers, inclusive, and removal of the solvent gives 4.57 grams (55% yield) of methyl (7S)-N-acetyl-2,3,4-tri-O-acetyl-7-deoxy-7-(2-hydroxyethylthio)-α-thiolincosaminide as a colorless solid. It is obtained as needles on crystallization from ethyl acetate-Skellysolve B, m.p. 226°–8° C., undepressed on admixture with material derived from 2-hydroxyethyl methyl sulfide (Example 10, Part A-10a of U.S. Pat. No. 3,915,954) and identical with this compound in I.R. and N.M.R. spectra.

Part B-2 - Methyl (7S)-7-deoxy-(2-hydroxyethylthio)-α-thiolincosaminide

Methyl (7S)-7-deoxy-(2-hydroxyethylthio)-α-thiolincosaminide can be obtained from methyl (7S)-N-acetyl-2,3,4-tri-O-acetyl-7-deoxy-7-(2-hydroxyethylthio)-α-thiolincosaminide by following the procedure of Example 1, Part B-1 of U.S. Pat. No. 3,915,954.

Part C-2 - (7S)-7-deoxy-(2-hydroxyethylthio)lincomycin hydrochloride (7S)-7-deoxy-(2-hydroxyethylthio)lincomycin hydrochloride can be obtained from methyl (7S)-7-deoxy-(2-hydroxyethylthio)-α-thiolincosaminide by following the procedure of Example 1, Part C-1 of U.S. Pat. No. 3,915,954.

EXAMPLE 3

Part A-3 - Methyl (7S)-N-acetyl-7-deoxy-7-(2-hydroxyethylthio)lincosaminide

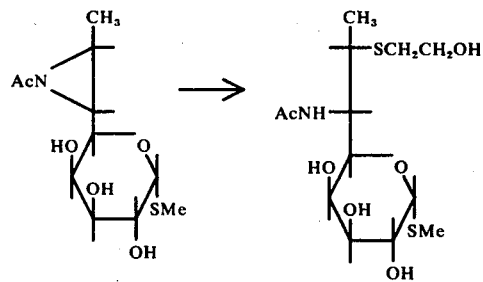

5.0 Grams (1 molar equivalent) of methyl (6R,7R)-N-acetyl-6,7-aziridino-6-deamino-7-deoxy-α-thiolincosaminide is dissolved in 50 grams (35 molar equivalents) of 2-hydroxyethanethiol by stirring in an oil bath at 100° C. 7.56 Grams (7.2 ml., 7 molar equivalents) of glacial acetic acid are added, and the mixture heated at 100° C. for 17 hours, with the exclusion of moisture. At the end of this time, volatile materials are removed from the reaction solution by distillation under high vacuum (ca. 0.2 mm Hg) from an oil-bath at 100° C., yielding a syrupy residue showing by tlc [silica gel, methanol-chloroform (1:5 v/v)] a major zone of $R_f$ 0.28. Chromatography on silica gel in methanol-methylene chloride (1:8, v/v) (column dimensions 5.8 × 99 cm., 1200 grams of silica) gives the desired material in fractions nos. 152-255, inclusive (collecting 50 ml. fractions after a forerun of 1450 ml.) obtained as a non-crystalline solid (2.98 grams) on removal of the solvent. Rechromatography to remove additional traces of impurity is conducted with a high performance liquid chromatogram (silica gel, 241 grams, dimensions 2.8 × 104 mm) in methanol-methylene chloride (1:8, v/v) at a flow rate of 3.5 ml./min. under a pressure of 12 p.s.i. Fractions of 50 ml. are collected, and the desired crude material is present in fractions nos. 21-27, inclusive, and is isolated as a colorless amorphous solid on removal of solvent in vacuo.

Part B-3 - Methyl (7)-N-acetyl-2,3,4-tri-0-acetyl-7-deoxy-7-(2-acetoxyethylthio)-α-thiolincosaminide

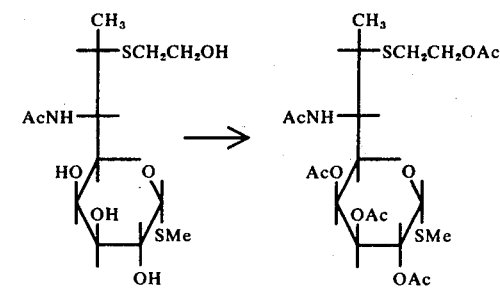

The solid obtained from Example 3, Part A-3, is acetylated by dissolving in pyridine (10 ml.), adding acetic anhydride (5 ml.), and allowing the solution to stand at room temperature for 48 hours with exclusion of moisture. Volatile materials are removed in vacuo, and the residue is dissolved in methylene chloride, washed with dilute aqueous hydrochloric acid, water, saturated aqueous sodium hydrogen carbonate, water, and dried over anhydrous sodium sulfate. Removal of the solvent in vacuo yields a colorless solid showing a single zone of $R_f$ 0.44 by tlc [silica gel, acetone:Skellysolve B (1:1, v/v)].

The above solid is subjected to countercurrent distribution in the system ethanol-water-ethyl acetatecyclohexane (1:1:1:3, v/v) to yield a major product at a K value of 0.48. Combination of material from tubes 130-199, inclusive, after 500 transfers, and removal of the solvent in vacuo gives 1.60 grams (16%) of methyl (7S)-N-acetyl-2,3,4-tri-0-acetyl-7-deoxy-7-(2-acetoxyethylthio)-α-thiolincosaminide as a colorless solid. It is obtained as needles on crystallization from ethyl acetate-Skellysolve B, m.p. 206–207° C., undepressed on admixture with material derived from 2-acetoxyethyl methyl sulfide (Example 10, Part A-10B, of U.S. Pat. No. 3,915,954) and from ethylene sulfide (Example 1, Part A-1 of U.S. Pat. No. 3,767,649) and identical with this compound in the I.R. and N.M.R. spectra.

Part C-3 - Methyl (7S)-7-deoxy-7-(2-hydroxyethylthio)-α-thiolincosaminide

Methyl (7S)-7-deoxy-7-(2-hydroxyethylthio)-α-thiolincosaminide can be obtained from methyl (7S)-N-acetyl-2,3,4-tri-0-acetyl-7-deoxy-7-(2-acetoxyethylthio)-α-thiolincosaminide by following the procedure of Example 1, Part B-1 of U.S. Pat. No. 3,767,649.

Part D-3 - (7S)-7-deoxy-7-(2-hydroxyethylthio)lincomycin hydrochloride (7S)-7-Deoxy-7-(2-hydroxyethylthio)lincomycin hydrochloride can be obtained from methyl (7S)-7-deoxy-7-(2hydroxyethylthio)-α-thiolincosaminide by following the procedure of Example 1, Part C-1 of U.S. Pat. No. 3,915,954.

EXAMPLE 4

Following the procedure above of Example 1, Part A-1, but replacing the 2-methoxyethanethiol as used herein, by any other thiol shown in Table I, there can be obtained the corresponding methyl (7S)-N-acetyl- 2,3,4-tri-0-acetyl-7-deoxy-7-(ω-substituted alkylthio)-α-thiolincosaminide.

I claim:

1. A process for making compounds of the formula:

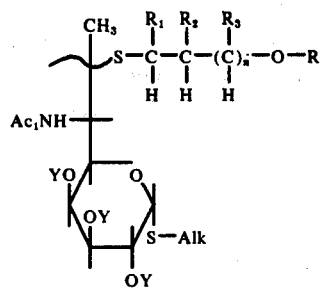

wherein Alk is alkyl of not more than 4 carbon atoms; $Ac_1$ and Y is carboxacyl; $R_1$ is hydrogen, methyl or ethyl; $R_2$ is hydrogen, methyl or ethyl; $R_3$ is hydrogen, methyl or ethyl; n is 0 or 1; and R is hydrogen, alkyl of 1 to 6 carbon atoms, inclusive, or aralkyl of 7 to 12 carbon atoms, inclusive; which comprises heating at a temperature of from about 25° C. to about 180° C. a compound of the formula:

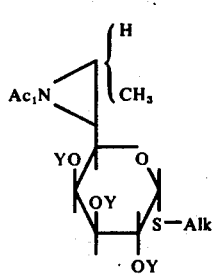

wherein $Ac_1$ and Y are carboxacyl; and Alk is alkyl of not more than 4 carbon atoms, with a thiol of the formula:

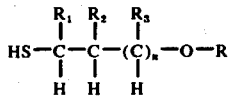

wherein $R_1$ is hydrogen, methyl or ethyl; $R_2$ is hydrogen, methyl or ethyl; $R_3$ is hydrogen, methyl or ethyl; n is 0 or 1; and R is hydrogen, alkyl of 1 to 6 carbon atoms, inclusive, or aralkyl of 7 to 12 carbon atoms, inclusive, in the presence of an anhydrous lower hydrocarbon carboxylic acid.

2. A process according to claim 1 for making compounds of the formula:

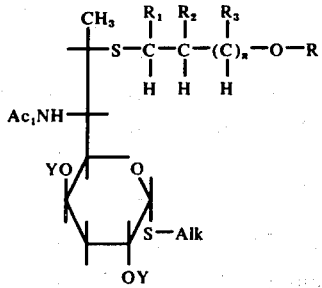

wherein Alk, $Ac_1$, Y, $R_1$, $R_2$, $R_3$, n, and R are as given in claim 1; which comprises heating at a temperature of from about 25° C. to about 180° C. a compound of the formula:

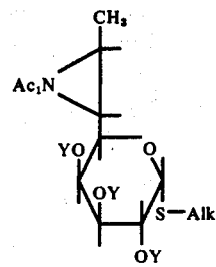

wherein $Ac_1$, Y, and Alk are as given in claim 1, with a thiol of the formula:

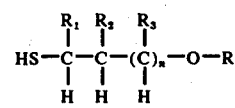

wherein R, $R_1$, $R_2$, $R_3$ and n are as given in claim 1, in the presence of an anhydrous lower hydrocarbon carboxylic acid.

3. The process of claim 2 in which Y and $Ac_1$ are acetyl.

4. The process of claim 2 in which R is hydrogen.

5. The process of claim 2 in which R is alkyl of 1 to 6 carbon atoms.

6. The process of claim 2 in which $R_1$, $R_2$, and $R_3$ are hydrogen.

7. The process of claim 2 in which the anhydrous lower hydrocarbon carboxylic acid is glacial acetic acid.

8. The process of claim 2 wherein methyl (6R,7R)-N-acetyl-2,3,4-tri-0-acetyl-6,7-aziridino-6-deamino-7-deoxy-α-thiolincosaminide is reacted with 2-hydroxyethanethiol and there is obtained methyl (7S)-N-acetyl-2,3,4-tri-0-acetyl-7-deoxy-7-(2-hydroxyethylthio)-α-thiolincosaminide.

9. The process of claim 7 wherein methyl (6R,7R)-N-acetyl-2,3,4-tri-0-acetyl-6,7-aziridino-6-deamino-6-deoxy-α-thiolincosaminide is reacted with 2-hydroxyethanethiol and there is obtained methyl (7S)-N-acetyl-2,3,4-tri-0-acetyl-7-deoxy-7-(2-hydroxyethylthio)-α-thiolincosaminide.

10. A process for the production of a compound of the formula:

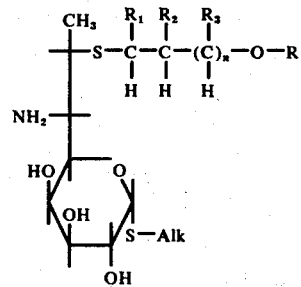

wherein Alk is alkyl of not more than 4 carbon atoms; $R_1$ is hydrogen, methyl or ethyl; $R_2$ is hydrogen, methyl or ethyl; $R_3$ is hydrogen, methyl or ethyl; n is 0 or 1; and R is hydrogen, alkyl of 1 to 6 carbon atoms, inclusive, or aralkyl of 7 to 12 carbon atoms, inclusive; which comprises heating at a temperature of from about 25° C. to about 180° C. a compound of the formula:

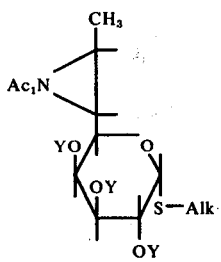

wherein Alk is defined as above, and wherein $Ac_1$ and Y are carboxacyl, with a thiol of the formula:

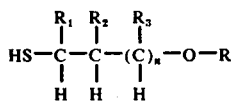

wherein R, $R_1$, $R_2$, $R_3$ and n are defined as above, in the presence of an anhydrous lower hydrocarbon carboxylic acid to form

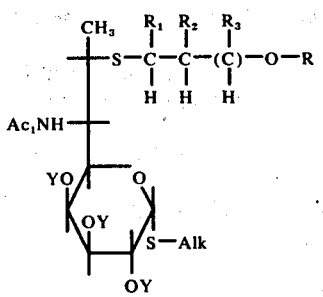

wherein R, $R_1$, $R_2$, $R_3$, $Ac_1$, Y, Alk and n are defined as above, deacylating the latter to form the desired compound.

11. The process of claim 10 in which the anhydrous lower hydrocarbon carboxylic acid is glacial acetic acid.

12. The process of claim 10, wherein the starting material is methyl (6R,7R)-N-acetyl-2,3,4-tri-O-acetyl-6,7-aziridino-6-deamino-7-deoxy-α-thiolincosaminide, the thiol is 2-hydroxyethanethiol and the end product is methyl (7S)-7-deoxy-(2-hydroxyethylthio)-α-thiolincosaminide.

13. The process of claim 11, wherein the starting material is methyl (6R,7R)-N-acetyl-2,3,4-tri-O-acetyl-6,7-aziridino-6-deamino-7-deoxy-α-thiolincosaminide, the thiol is 2-hydroxyethanethiol and the end product is methyl (7S)-7-deoxy-(2-hydroxyethylthio)-α-thiolincosaminide.

14. A process for the production of a compound of the formula:

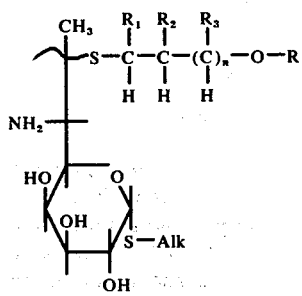

wherein Alk is alkyl of not more than 4 carbon atoms; $R_1$ is hydrogen, methyl or ethyl; $R_2$ is hydrogen, methyl or ethyl; $R_3$ is hydrogen, methyl or ethyl; n is 0 or 1; and R is hydrogen, alkyl of 1 to 6 carbon atoms, inclusive, or aralkyl of 7 to 12 carbon atoms, inclusive; which comprises heating at a temperature of from about 25° C. to about 180° C. a compound of the formula:

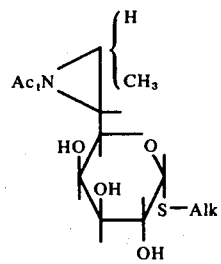

wherein Alk is defined as above, and wherein $Ac_1$ is carboxacyl, with a thiol of the formula:

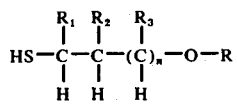

wherein R, $R_1$, $R_2$, $R_3$ and n are defined as above, in the presence of an anhydrous lower hydrocarbon carboxylic acid to form

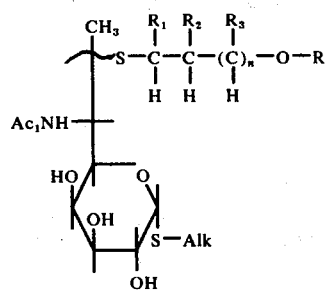

wherein R, $R_1$, $R_2$, $R_3$, $Ac_1$, Alk and n are defined as above; acylating the alcoholic hydroxyl groups of said compound to form the corresponding alkyl N-acyl-2,3,4-tri-O-acyl-7-deoxy-7-(ω-acyloxyalkylthio)-α-thiolincosaminide when R is hydrogen, alkyl N-acyl-2,3,4-tri-O-acyl-7-deoxy-7-(ω-alkoxyalkylthio)-α-thiolincosaminide when R is alkyl of 1 to 6 carbon atoms, inclusive, or alkyl N-acyl-2,3,4-tri-O-acyl-7-deoxy-7-(ω-aralkoxyalkylthio)-α-thiolincosaminide when R is aralkyl of 7 to 12 carbon atoms, inclusive, and deacylating the latter to form the desired compound.

15. A process according to claim 14 for making compounds of the formula:

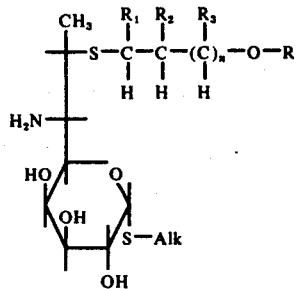

wherein Alk, R, $R_1$, $R_2$, $R_3$ and n are as given in claim 14; which comprises heating at a temperature of from about 25° C. to about 180° C. a compound of the formula:

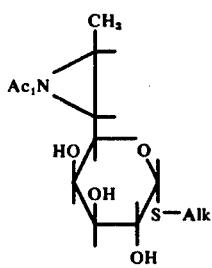

wherein $Ac_1$ and Alk are as given in claim 14, with a thiol of the formula:

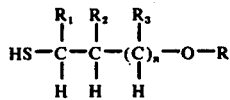

wherein R, $R_1$, $R_2$, $R_3$ and n are as given in claim 14, in the presence of an anhydrous lower hydrocarbon carboxylic acid, to form

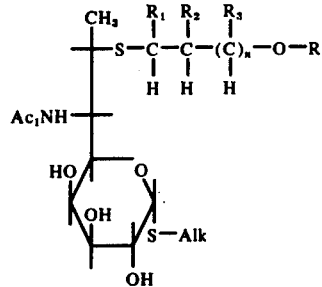

wherein R, $R_1$, $R_2$, $R_3$, $Ac_1$, Alk and n are as defined in claim 14, acylating the alcoholic hydroxyl groups of said compound to form the corresponding alkyl (7S)-N-acyl-2,3,4-tri-0-acyl-7-deoxy-7-(ω-acyloxyalkylthio)-α-thiolincosaminide when R is hydrogen, alkyl (7S)-N-acyl-2,3,4-tri-0-acyl-7-deoxy-7-(ω-alkoxyalkylthio)-α-thiolincosaminide when R is alkyl of 1 to 6 carbon atoms, inclusive, or alkyl (7S)-N-acyl-2,3,4-tri-0-acyl-7-deoxy-7-(ω-aralkoxyalkylthio)-α-thiolincosaminide when R is aralkyl of 7 to 12 carbon atoms, inclusive, and deacylating the latter to form the desired compound.

16. The process of claim 15 in which the anhydrous lower hydrocarbon carboxylic acid is glacial acetic acid.

17. The process of claim 15, wherein the starting material is methyl (6R,7R)-N-acetyl-6,7-aziridino-6-deamino-7-deoxy-α-thiolincosaminide, the thiol is 2-hydroxyethanethiol and the end product is methyl (7S)-(2-hydroxyethylthio)-7-deoxy-α-thiolincosaminide.

18. The process of claim 16, wherein the starting material is methyl (6R,7R)-N-acetyl-6,7-aziridino-6-deamino-7-deoxy-α-thiolincosaminide, the thiol is 2-hydroxyethanethiol and the end product is methyl (7S)-(2-hydroxyethylthio)-7-deoxy-α-thiolinocosaminide.

* * * * *

UNITED STATES PATENT OFFICE
CERTIFICATE OF CORRECTION

Page 1 of 2

Patent No. 4,031,304         Dated June 21, 1977

Inventor(s) Brian Bannister

It is certified that error appears in the above-identified patent and that said Letters Patent are hereby corrected as shown below:

Column 1, line 50:   "carbpon" should read -- carbon --.
Column 3, line 37 (In formula IVa):   "R$^3$" should read -- R$_3$ --.
Column 5, line 51:   "3-thiol," should read -- 1-thiol, --.
Column 6, line 19:   "2- [(" should read -- 2-{[( --.
Column 6, line 19:   "methyl propane" should read -- methyl}propane --.
Column 6, line 23:   "2- [(" should read -- 2-{[( --.
Column 6, line 23:   "methyl butane" should read -- methyl}butane --.
Column 6, line 28:   "propane:2-" should read -- propane-2- --.
Column 6, line 31:   "2- [(" should read -- 2-{[( --.
Column 6, line 31:   "methyl propane" should read -- methyl}propane --.
Column 6, line 35:   "2- [(" should read -- 2-{[( --.
Column 6, line 35:   "methyl butane" should read -- methyl}butane --.
Column 6, line 36:   "1-[-(" should read -- 1-[( --.
Column 6, line 43:   "2- [(" should read -- 2-{[( --.
Column 6, line 43:   "methyl propane" should read -- methyl}propane --.
Column 6, line 48:   "2- [(" should read -- 2-{[( --.
Column 6, line 48:   "methyl butane" should read -- methyl}butane --.
Column 6, line 57:   "2- [(" should read -- 2-{[( --.
Column 6, line 57:   "methyl propane" should read -- methyl}propane --.
Column 6, line 62:   "2- [(" should read -- 2-{[( --.
Column 6, line 62:   "methyl butane" should read -- methyl}butane --.
Column 6, line 67:   "2-(ar" should read -- 2-[(ar --.
Column 6, line 68:   "1-[(arm-methylnaphthyl" should read -- 1-[(ar-methylnaphthyl --.
Column 7, line 3:   "2- [(" should read -- 2-{[( --.
Column 7, line 3:   "methyl propane" should read -- methyl}propane --.
Column 7, line 8:   "2- [ar" should read -- 2-{[(ar --.
Column 7, line 8:   "methyl butane" should read -- methyl}butane --.
Column 7, line 17:   "2- [(" should read -- 2-{[( --.
Column 7, line 17:   "methyl propane" should read -- methyl}propane --.
Column 7, line 21:   "2- [(" should read -- 2-{[( --.

UNITED STATES PATENT OFFICE
CERTIFICATE OF CORRECTION

Patent No. 4,031,304  Dated June 21, 1977

Inventor(s) Brian Bannister

It is certified that error appears in the above-identified patent and that said Letters Patent are hereby corrected as shown below:

Column 7, line 21: "methyl butane" should read -- methyl}butane --.
Column 9, line 3: "(6R,7)R-" should read -- (6R,7R)- --.
Column 12, line 46: "(IIB)" should read -- (IIb) --.
Column 15, line 1: "Skellysolve B" should read -- Skellysolve B® --.
Column 16, line 28: "Skellysolve B" should read -- Skellysolve B® --.
Column 16, line 35: "(16%)" should read -- (16% yield) --.
Column 16, line 39: "Skellysolve B" should read -- Skellysolve B® --.
Column 16, line 60: "(2hydroxyethylthio)" should read -- (2-hydroxyethylthio) --.
Column 16, line 67: "herein" should read -- therein --.

Column 19, line 27:
"
$$\begin{array}{ccc} R_1 & R_2 & R_3 \\ | & | & | \\ S-C - C-(C)-O-R \\ | & | & | \\ H & H & H \end{array}$$
" should read --
$$\begin{array}{ccc} R_1 & R_2 & R_3 \\ | & | & | \\ S-C - C-(C)_n-O-R \\ | & | & | \\ H & H & H \end{array}$$
--.

Signed and Sealed this

Third Day of November 1981

[SEAL]

Attest:

GERALD J. MOSSINGHOFF

Attesting Officer  Commissioner of Patents and Trademarks